United States Patent [19]

Linn et al.

[11] Patent Number: 4,797,272

[45] Date of Patent: Jan. 10, 1989

[54] WATER-IN-OIL MICROEMULSIONS FOR COSMETIC USES

[75] Inventors: Edwards E. Linn, Carmel; Michael P. West, Indianapolis, both of Ind.

[73] Assignee: Eli Lilly and Company, Indianapolis, Ind.

[21] Appl. No.: 798,501

[22] Filed: Nov. 15, 1985

[51] Int. Cl.⁴ .......................... A61K 7/42; A61K 7/44; A61K 7/48; A61K 9/10

[52] U.S. Cl. ....................................... 424/59; 252/311; 424/60; 514/847; 514/937

[58] Field of Search .................. 424/59; 514/847, 937

[56] References Cited

U.S. PATENT DOCUMENTS

| | | | |
|---|---|---|---|
| 3,778,381 | 12/1973 | Rosano et al. | 252/311 |
| 3,917,830 | 11/1975 | Davis et al. | 424/243 |
| 4,146,499 | 3/1979 | Rosano | 252/186 |
| 4,563,346 | 1/1986 | Deckner | 424/60 |
| 4,595,586 | 6/1986 | Flom | 424/60 |
| 4,597,963 | 7/1986 | Deckner | 424/60 |
| 4,604,281 | 8/1986 | Deckner | 424/60 |
| 4,608,392 | 8/1986 | Jacquet | 424/60 |
| 4,663,155 | 5/1987 | Murray et al. | 424/60 |
| 4,663,156 | 5/1987 | Clum et al. | 424/60 |

FOREIGN PATENT DOCUMENTS

| | | | |
|---|---|---|---|
| 2509989 | 1/1983 | France | 424/60 |
| 2098865 | 12/1982 | United Kingdom | 424/243 |

OTHER PUBLICATIONS

Jayakrishnan et al., "Microemusions:Evolving Technology for Cosmetic Applications", *J. Soc. Cosmet. Chem.* 34, 335–350, (1983).

*Emulsions and Emulsion Technology*, Part 1, Ed. Kenneth J. Lissant, Marcel Dekker, Inc. New York, Chapter 3, "Microemulsions", (1974).

*Primary Examiner*—Dale R. Ore
*Attorney, Agent, or Firm*—Kenyon & Kenyon

[57] ABSTRACT

The present invention provides water-in-oil microemulsions suitable for cosmetic uses containing moisturizing agents or sunscreens.

20 Claims, No Drawings

WATER-IN-OIL MICROEMULSIONS FOR COSMETIC USES

BACKGROUND OF THE INVENTION

An emulsion is a dispersed system containing at least two immiscible liquid phases, one of which is dispersed in the form of small droplets throughout the other, and an emulsifying agent in order to improve the stability of the system.

There are two types of emulsions depending on the droplet size of the liquids present in the emulsions. Macroemulsions do not permit light to pass through them and have droplets with average diameters of about 10 to about 1000 microns. As such, these emulsions typically appear milky white. Microemulsions are stable systems consisting of droplets which are significantly smaller, being approximately 0.14 microns in diameter on the average. As such, microemulsions are translucent, and routinely transparent, in nature. Microemulsions are an extraordinary type of emulsion that forms spontaneously. Products consisting of these systems are valued for their stability and small particle size, which affords microemulsions special consideration in the market place. Additional information on microemulsions and their properties may be obtained from *Emulsions and Emulsion Technology* Part I, ed. Kenneth J. Lissant, Marcel Dekker, Inc., New York, Chapter 3 "Microemulsions" (1974).

Emulsions have a variety of uses, most notably as vehicles for the delivery of medicines. In particular, microemulsions are known to deliver pharmacologically active agents as disclosed in U.K. Pat. No. 2,098,865. Microemulsions are also known to provide injectible compositions containing an anaesthetic, as disclosed in U.S. Pat. No. 3,917,830, and are known as carriers for oxygen absorbing fluorinated organic compounds, as disclosed in U.S. Pat. No. 3,778,381. Jayakrishnan et al. in *J. Soc. Cosmet. Chem.* 34, 335-350 (1983) disclose the delivery of hydrocortisone with microemulsions. Finally, U.S. Pat. No. 4,146,499 discloses oil-in-water microemulsions allegedly capable of containing a variety of hydrophobic substances including certain cosmetics.

SUMMARY OF THE INVENTION

The present invention provides new microemulsion compositions. More specifically, the invention provides a water-in-oil microemulsion composition comprising from about 5% by weight to about 35% by weight of a moisturizer, from about 20% by weight to about 80% by weight of surfactants, from about 10% by weight to about 70% by weight of oils, and from about 5% by weight to about 50% by weight of skin humectants and having an average droplet size in the range of about 0.001 microns to about 0.2 microns in diameter.

The present invention also provides a water-in-oil microemulsion composition comprising from about 1% by weight to about 8% by weight of a sunscreen, from about 15% by weight to about 79% by weight of surfactants, from about 15% by weight to about 79% by weight of oils, and from about 5% by weight to about 50% by weight of skin humectants and having an average droplet size in the range of about 0.001 microns to about 0.2 microns in diameter.

DETAILED DESCRIPTION OF THE INVENTION

Typically, one of the two immiscible liquids in an emulsion is aqueous while the other is an oil. Emulsions may be classified depending on which liquid forms the dispersed phase and which liquid forms the dispersion medium. An emulsion in which oil is dispersed as droplets throughout the aqueous phase is termed an oil-in-water emulsion. When water is the dispersed phase and an oil is the dispersion medium, a water-in-oil emulsion exists. Whether the aqueous phase or the oil phase becomes the dispersed phase, or is the dispersion medium, depends primarily on the emulsifying agent used and the relative amounts of the two liquid phases. Emulsified lotions or creams contemplated herein are water-in-oil microemulsions wherein the continuous phase is oil.

A water-in-oil microemulsion of the invention comprises from about 5% by weight to about 35% by weight of a moisturizer, from about 20% by weight to about 80% by weight of surfactants, from about 10% by weight to about 70% by weight of oils, and from about 5% by weight to about 50% by weight of skin humectants. The composition will preferably contain from about 15% by weight to about 30% by weight of a moisturizer, from about 20% by weight to about 35% by weight of surfactants and cosurfactants, from about 20% by weight to about 55% by weight of oils and from about 20% by weight to about 35% by weight of skin humectants.

Another water-in-oil microemulsion of the invention comprises from about 1% by weight to about 8% by weight of a sunscreen, from about 15% by weight to about 79% by weight of surfactants, from about 15% by weight to about 79% by weight of oils, and from about 5% by weight to about 50% by weight of skin humectants. The composition will preferably contain from about 2% by weight to about 6% by weight of a sunscreen, from about 20% by weight to about 35% by weight of surfactants and cosurfactants, from about 20% by weight to about 55% by weight of oils and from about 20% by weight to about 35% by weight of skin humectants.

In one aspect of the present invention, one or more moisturizers may be incorporated into the present microemulsions. Exemplary moisturizers are well known in the art and include Polawax, jojoba oil, long chain hydrocarbons such as squalane, and long chain esters such as isopropyl myristate. Moisturizers are typically incorporated into the oil phase during the preparation of the microemulsions.

In another embodiment of the invention one or more sunscreens may be incorporated into the present microemulsions. A variety of sunscreens may be employed including the p-aminobenzoic acid derivatives such as p-(2-ethylhexyl)dimethylaminobenzoate, and benzophenone derivatives such as benzophenone-3. The exact amount of sunscreen employed in the present compositions will vary depending on the degree of protection desired from the sun's harmful rays.

The present composition may also contain both ( moisturizers and sunscreens in combination at concentrations similar to those described above when each ingredient is used alone.

A variety of surfactants may be employed in the compositions of the invention. These surfactants are well known to formulation chemists skilled in the art. Surfactants may be cationic, nonionic or anionic in nature. Preferably, nonionic surfactants are employed in the present microemulsions because they are nonirritating to skin. Anionic surfactants may also be employed, but care should be taken to make the resulting compositions as nonirritating as possible. Suitable surfactants include esters of aliphatic carboxylic acids having from 12 to 18 carbon atoms in combination with either a polyoxyethylene (4-20) sorbitan ether or other sorbitan ether substance. Also, esters of unsaturated carboxylic acids having from 12 to 18 carbon atoms together with either a polyoxyethylene (4-20) sorbitan ether or other sorbitan ether substance may be employed as surfactants. Finally, combinations of the aliphatic and unsaturated carboxylic acid esters described above may be employed in combination with either sorbitan derivative also described hereinbefore.

The compositions of the invention may also contain one or more cosurfactants in addition to the surfactants described above. Exemplary cosurfactants suitable for use herein include fatty aliphatic alcohols having from 12 to 18 carbon atoms, such as cetyl alcohol or myristyl alcohol, short chain alkyl alcohols having from 1 to 3 carbon atoms with or without branching, or mixtures of these two ingredients. Typically, long chain alkyl alcohol cosolvents are employed in water-in-oil microemulsions.

A variety of skin compatible oils may also be employed in a composition of the invention which are known and commonly used by those of ordinary skill in the art. Exemplary oils include hydrocarbon straight chain alkyl compounds having from 12 to 18 carbon atoms, hydrocarbon branched alkyl compounds having from 12 to 30 carbon atoms, esters of straight alkyl chain hydrocarbons having from 12 to 18 carbon atoms together with a fatty alcohol having from 3 to 14 carbon atoms or a vegetable oil containing mono, di- or triglycerides, and cyclic dimethyl polysiloxane compounds such as cyclomethicone.

The combinations of the invention will also contain one or more suitable skin compatible humectants. These humectants are polar in nature and include deionized water, propylene glycol, glycerine, sorbitol or other polyhydric alcohols.

All cosmetic compositions must be protected against the growth of potentially harmful microorganisms, and therefore preservatives are added as a routine. While it is in the aqueous phase that microorganisms tend to grow, microorganisms can also reside in the oil phase. As such, preservatives which have solubility in both water and oil are preferably employed in the present compositions. Generally from one tenth of one percent by weight to one percent by weight of preservatives are adequate. The traditional preservatives for cosmetics and pharmaceuticals are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives for a preferred emulsion product of this invention are methyl and propyl para-hydroxybenzoates, imidazolidinyl urea, and quaternium-15. The preservatives should be selected having regard for the use of the composition and possible incompatibilities between the preservatives and the other ingredients in the emulsion.

As noted above, the compositions of the invention are translucent, and typically transparent since the average droplet size of a microemulsion is very small and does not reflect light, as compared to the macroemulsion average droplet size, which is from about 10 microns or more in diameter. As such, the compositions of the invention will have a droplet size in the range of about 0.001 microns to about 0.2 micron in diameter, more typically in the range of about 0.01 microns to about 0.14 microns in diameter.

The compositions of the invention may be prepared by procedures well known to formulation chemists. Typically, an oil phase is prepared by combining all hydrophobic components, as well as the water-insoluble solids, in a container and heating the resulting mixture under agitation until all the ingredients are dissolved. In a separate container, an aqueous phase is prepared by combining all of the hydrophilic components, as well as the oil-insoluble solids, and heating the resulting mixture under constant stirring until the mixture is homogeneous. The surfactants and cosurfactants are separately combined and mixed until homogeneous, and heat may be applied if necessary. The three phases thus prepared are combined and stirred until homogeneous and the solution becomes clear when allowed to stand at room temperature. The composition is finally allowed to stand for approximately 24 hours in order for the composition to achieve equilibrium. The composition may be transferred to appropriate containers for storage until needed for application to individuals in need of a microemulsion of the invention.

The microemulsion compositions of the invention may also contain one or more pigments so as to provide coloration to the composition, and a fragrance to make the composition soothing to the olfactory system. The amount of these ingredients present in the composition will depend on the specific effect desired.

The compositions of the invention are useful for a variety of purposes, especially for protecting the skin's surface. Such protection may be from the sun, wind, and rain. The present microemulsions are particularly well suited for use as moisturizing agents, and this is the primary use contemplated for the microemulsion. To assist in protecting skin from the sun, a sunscreen may be incorporated into the microemulsions of the invention.

The microemulsion compositions of the present invention provide superior results when applied to skin since they leave little residue on the surface of the skin following their application. The compositions promote the penetration of moisturizers and sunscreens into the skin, thereby allowing the delivery of an increased dose of these agents to the subject. Further, the compositions are not irritating to the skin.

It is important from a commercial standpoint that the compositions of the invention remain stable over a range of temperatures and under various conditions. For example, these compositions may be used under warm, humid conditions in the summer, or under cold, dry conditions in the winter when the microemulsion would typically contain a moisturizing agent. While such stability is important from an esthetic point of view, this generally does not substantially affect the operability of the microemulsions of the invention.

The following Examples illustrate formulations of the invention, and methods for their preparation. The Examples are not intended to be limiting to the scope of the present invention in any respect and should not be so construed.

EXAMPLE 1

An oil phase was prepared by combining 1000 g (25.0%) of Silicone 344 Fluid (cyclomethicone from Dow Corning Corp., Midland, Mich.), 788 g (19.7%) of Robane (squalane from Robeco Chemicals, Inc., New York, N.Y.), 80 g (2.0%) of Polawax and 120 g (3.0%) of isopropyl myristate and stirring the resulting mixture under heat until homogeneous. To the oil phase was added 6 g (0.15%) of methylparaben and 6 g (0.15%) of propylparaben and the resulting mixture was heated until the two paraben derivatives were dissolved. In a separate container a water phase was prepared by dissolving 8 g (0.2%) of Germall 115 (imidazolidinyl urea from Sutton Laboratories, Inc., Chatham, N.J.) in a solution of 80 g (2.0%) of glycerine and 912 g (22.8%) of deionized water. The water and oil phases were combined. To the resulting mixture was added 1000 g (25.0%) of Tween 21 (polysorbate 21 from ICI Americas, Inc., Wilmington, Del.) at room temperature and the mixture was allowed to equilibrate overnight prior to transferring the resulting water-in-oil microemulsion composition into appropriate container for storage.

EXAMPLE 2

A water-in-oil microemulsion composition of the invention was prepared according to the procedure of Example 1 containing the following ingredients:

| Phase | Ingredient | Weight (g) | Weight % |
|---|---|---|---|
| Oil | Silcone 344 Fluid | 800 | 20.0 |
| | Robane | 588 | 14.7 |
| | Polawax | 80 | 2.0 |
| | isopropyl myristate | 120 | 3.0 |
| | jojoba oil | 400 | 10.0 |
| Water | deionized water | 832 | 20.8 |
| | glycerine | 160 | 4.0 |
| | methylparaben | 6 | 0.15 |
| | propylparaben | 6 | 0.15 |
| | Germall 115 | 8 | 0.2 |
| Surfactant | T-Maz 21 (polysorbate 21 from Mazer Chemicals Inc., Gurnee, Illinois) | 1000 | 25.0 |

EXAMPLE 3

A water-in-oil microemulsion of the invention was prepared according the the general procedure of Example 1 containing the following ingredients:

| Phase | Ingredient | Weight (g) | Weight % |
|---|---|---|---|
| Oil | Silcone 344 Fluid | 200 | 20.0 |
| | Robane | 129 | 12.9 |
| | jojoba oil | 100 | 10.0 |
| | isopropyl myristate | 30 | 3.0 |
| | propylparaben | 1 | 0.1 |
| | propylene glycol | 20 | 2.0 |
| | myristyl alcohol | 10 | 1.0 |
| | cetyl alcohol | 6 | 0.6 |
| | polysorbate 60 | 4 | 0.4 |
| Water | deionized water | 244 | 24.4 |
| | Germall 115 | 3 | 0.3 |
| | methylparaben | 3 | 0.3 |
| Surfactant | polysorbate 21 | 250 | 25.0 |

EXAMPLE 4

Following the procedure outlined in Example 3, the following ingredients were formulated to provide a water-in-oil microemulsion of the invention.

| Phase | Ingredient | Weight (g) | Weight % |
|---|---|---|---|
| Oil | Silicone 344 Fluid | 800 | 20.0 |
| | Robane | 594 | 14.85 |
| | isopropyl myristate | 120 | 3.0 |
| | jojoba oil | 400 | 10.0 |
| Water | glycerine | 80 | 2.0 |
| | deionized water | 904 | 22.6 |
| | propylparaben | 6 | 0.15 |
| | methylparaben | 6 | 0.15 |
| | Germall 115 | 8 | 0.20 |
| Surfactant | sodium dodecyl sulfate | 2 | 0.05 |
| | T-Maz 21 | 1080 | 27.0 |

Two water-in-oil microemulsions of the invention were prepared containing a sunscreen. The preparation of these compositions is illustrated below.

EXAMPLE 5

An oil phase was prepared by combining 260 g (26.0%) of Silicone 344 Fluid, 157 g (15.7%) of Robane, 30 g (3.0%) of isopropyl myristate, 30 g (3.0%) of Escalol 507 (p-(2-ethylhexyl)dimethylaminobenzoate) and 20 g (2.0%) of benzophenone-3, and heating the resulting mixture with agitation until homogeneous. To the oil phase was added 1.5 g (0.1%) of propylparaben, and the resulting mixture was stirred until the propylparaben was dissolved. A water phase was prepared in a separate container by combining 248 ml (24.8%) of water and 1.5 g (0.15%) of methylparaben with 2.0 g (0.2%) of Germall 115 and heating the resulting mixture under agitation until homogeneous. The oil and water phases were combined and 250 g (25.0%) of T-Maz 21 was added thereto. The resulting composition was stirred until homogeneous and stored at room temperature until ready for use.

EXAMPLE 6

An oil phase was prepared by combining 1040 g (26.0%) of Silicone 344 Fluid, 628 g (15.7%) of Robane, 120 g (3.0%) of isopropyl myristate, 120 g (3.0%) of Escalol 507 and 80 g (2.0%) of benzophenone-3 in a suitable container. The mixture was heated and stirred until homogeneous. To the oil phase was added 6 g (0.15%) of methylparaben and 6 g (0.15%) of propylparaben with stirring until the mixture was homogeneous. A water phase was prepared in a separate container by combining 992 g (24.8%) of water with 8 g (0.2%) of Germall 115 and 8 g (0.2%) of sodium dodecyl sulfate. The oil and water phases were combined and 992 g (24.8%) of Tween 21 was added thereto. The mixture was stirred until homogeneous and stored at room temperature until ready for use.

Certain of the compositions of the invention were tested to demonstrate efficacy as moisturizing agents. The test was conducted on dry skin, and the compositions to be tested were used over a 3-week period, followed by a two-week regression period. Thirty-two subjects were used in the study to test the efficacy of the formulations. Subjects were divided into two groups of 16 and each member of one group randomly received the formulation of Example 1 on one leg and the formulation of Example 2 on the other leg. In the second group subjects randomly received the formulation of Example 4 on one leg. The study was carried out for seven weeks. For the first two weeks, skin was allowed to dry. For the next three weeks treatment was conducted, and the final two weeks were a regression period. Subjects with obvious skin conditions, extensive varicose veins, deep suntans, or conditions on their legs other than dry skin were excluded from the study. Subjects ranged in age from 18 to 45 years. Evaluations were performed blind by the same evaluator, when possible. Evaluations were done 7, 5 and 3 days before application, the initial day of treatment prior to application, and 1, 2, 3, 4, 7, 9, 10, 11, 15, 16, 17, 18, 21, 22, 23, 24, 25, 28, 30, 32 and 35 days after the initial application. Test formulations were applied to the leg(s) twice each day for three weeks, once in the morning in the laboratory and each evening at home on weekdays. All weekend applications (morning and evening) were performed at home. No other skin moisturizers except the test formulations were allowed during the course of the study. In addition, the subjects were not allowed to swim or sunbathe. Showers, baths, and water contact to the legs were also not allowed the mornings that evaluations were performed.

Evaluations were performed according to the following scale:

0 = smooth, no evidence of dryness
1 = slightly dry skin
2 = moderately dry skin; peeling
3 = severely dry skin; flaking, peeling
4 = extremely dry skin; flaking, peeling and/or fissures Results (mean dryness scores) of each of the formulations were compared to the untreated control and to the positive control groups. In addition, each product was evaluated for significant change from day 0 for each evaluation day in the study. This data is presented below in Table I as the average of the 16 subjects employed.

TABLE I

| Days After First Application | Moisturization Study Formulation of Example No. | | |
|---|---|---|---|
| | 1 | 2 | 4 |
| 0 | 3.0 | 3.0 | 3.0 |
| 1 | 2.0 | 1.8 | 2.3 |
| 2 | 0.9 | 0.8 | 1.3 |
| 3 | 0.3 | 0.4 | 0.8 |
| 4 | 0.5 | 0.3 | 0.6 |
| 7 | 0.1 | 0.1 | 0.7 |
| 9 | 0.5 | 0.4 | 0.4 |
| 10 | 0.3 | 0.2 | 0.5 |
| 11 | 0.1 | 0 | 0.5 |
| 15 | 0.9 | 0.7 | 1.3 |
| 16 | 0.2 | 0.2 | 0.8 |
| 17 | 0.2 | 0.3 | 0.4 |
| 18 | 0.1 | 0.1 | 0.3 |
| 21 | 0.1 | 0.1 | 0.3 |
| 22 | 0.5 | 0.3 | 0.9 |
| 23 | 0.2 | 0.3 | 1.3 |
| 24 | 0.5 | 0.3 | 1.1 |
| 25 | 0.5 | 0.4 | 1.1 |
| 28 | 0.9 | 0.6 | 1.6 |
| 30 | 1.1 | 1.0 | 1.9 |
| 32 | 1.8 | 1.8 | 2.3 |

TABLE I-continued

| Days After First Application | Moisturization Study Formulation of Example No. | | |
|---|---|---|---|
| | 1 | 2 | 4 |
| 35 | 2.4 | 2.4 | 2.8 |

The data generated from the preceding experiment indicate the effectiveness of the formulae of Examples 1 and 2 as moisturizers. The formula of Example 4 demonstrated moderate effectiveness as a moisturizer.

An additional moisturization study was conducted on the formulae of Examples 1 and 2. However, this data has not been supplied. Unusual and aberrant weather conditions which occurred during the test made interpretation of the results difficult.

We claim:

1. A stable water-in-oil microemulsion non-irritating moisturizing composition which when applied to skin promotes the penetration of moisturizers into the skin and leaves little residue on the surface of the skin following its application comprising from about 5% by weight to about 35% by weight of a moisturizer, from about 20% by weight to about 80% by weight of surfactants, from about 10% by weight to about 70% by weight of skin compatible oils, and from about 5% by weight to about 50% by weight of skin humectants and the composition having an average droplet size in the range of about 0.001 microns to about 0.2 microns in diameter, and wherein the compositon is adapted to promote the penetration of the moisturizers into the skin.

2. The composition of claim 1 comprising from about 15% by weight to about 30% by weight of a moisturizer, from about 20% by weight to about 35% by weight of surfactants and cosurfactants, from about 20% by weight to about 55% by weight, of oils and from about 20% by weight to about 35% by weight of skin humectants.

3. The composition of claim 2 comprising as additional ingredients from about 0.1% by weight to about 1.0% by weight of preservatives.

4. The composition of claim 3 consisting essentially of the following ingredients:

| Classification | Ingredient | Weight Percent |
|---|---|---|
| oil moisturizers | cyclomethicone | 25.0 |
| | squalane | 19.7 |
| | Polawax | 2.0 |
| | isopropyl myristate | 3.0 |
| skin humectants | water | 22.8 |
| | glycerine | 2.0 |
| surfactant | polysorbate 21 | 25.0 |
| preservatives | methylparaben | 0.15 |
| | propylparaben | 0.15 |
| | imidazolidinyl urea | 0.2 |

5. The composition of claim 3 consisting ssentially of the following ingredients:

| Classification | Ingredient | Weight Percent |
|---|---|---|
| oil moisturizers | cyclomethicone | 20.0 |
| | squalane | 14.7 |
| | Polawax | 2.0 |
| | isopropyl | 3.0 |

-continued

| Classification | Ingredient | Weight Percent |
| --- | --- | --- |
| | myristate | |
| | jojoba oil | 10.0 |
| skin humectants | water | 20.8 |
| | glycerine | 4.0 |
| surfactant | polysorbate 21 | 25.0 |
| preservatives | methylparaben | 0.15 |
| | propylparaben | 0.15 |
| | imidazolidinyl urea | 0.2 |

6. The composition of claim 3 consisting essentially of the following ingredients:

| Classification | Ingredient | Weight Percent |
| --- | --- | --- |
| oil | cyclomethicone | 20.0 |
| moisturizers | squalane | 12.9 |
| | isopropyl myristate | 3.0 |
| | jojoba oil | 10.0 |
| skin humectants | water | 24.4 |
| | propylene glycol | 2.0 |
| surfactants | polysorbate 21 | 25.0 |
| | myristyl alcohol | 1.0 |
| | cetyl alcohol | 0.6 |
| | polysorbate 60 | 0.4 |
| preservatives | methylparaben | 0.3 |
| | propylparaben | 0.1 |
| | imidazolidinyl urea | 0.3 |

7. The composition of claim 3 consisting essentially of the following ingredients:

| Classification | Ingredient | Weight Percent |
| --- | --- | --- |
| oil | cyclomethicone | 20.0 |
| moisturizers | squalane | 14.85 |
| | isopropyl myristate | 3.0 |
| | jojoba oil | 10.0 |
| skin humectants | water | 22.6 |
| | glycerine | 2.0 |
| surfactants | polysorbate 21 | 27.0 |
| | sodium dodecyl sulfate | 0.05 |
| preservatives | methylparaben | 0.15 |
| | propylparaben | 0.15 |
| | imidazolidinyl urea | 0.2 |

8. A stable water-in-oil microemulsion non-irritating sunscreen composition which when applied to skin promotes the penetration of sunscreen into the skin and leaves little residue on the surface of the skin following its application comprising from about 1% by weight to about 8% by weight of a sunscreen, from about 15% by weight to about 79% by weight of surfactants, from about 15% by weight to about 79% by weight of skin compatible oils, and from about 5% by weight to about 50% by weight of skin humectants and the composition having an average droplet size in the range of about 0.001 microns to about 0.2 microns in diameter, and wherein the composition is adapted to promote the penetration of sunscreen to the skin.

9. The composition of claim 8 comprising from about 2% by weight to about 6% by weight of a sunscreen, from about 20% by weight to about 35% by weight of surfactants and cosurfactants, from about 20% by weight to about 55% by weight of oils and from about 20% by weight to about 35% by weight of skin humectants.

10. A composition of claim 9 comprising as additional ingredients from about 15% by weight to about 20% by weight of moisturizers.

11. A composition of claim 10 comprising as additional ingredients from about 0.1% by weight to about 1.0% by weight of preservatives.

12. The composition of claim 11 consisting essentially of the following ingredients:

| Classification | Ingredient | Weight Percent |
| --- | --- | --- |
| oil | cyclomethicone | 26.0 |
| moisturizers | squalane | 15.7 |
| | isopropyl myristate | 3.0 |
| sunscreens | p-(2-ethylhexyl)-dimethylaminobenzoate | 3.0 |
| | benzophenone-3 | 2.0 |
| skin humectants | water | 24.8 |
| surfactant | polysorbate 21 | 25.0 |
| preservatives | methylparaben | 0.15 |
| | propylparaben | 0.15 |
| | imidazolidinyl urea | 0.2 |

13. The composition of claim 11 consisting essentially of the following ingredients:

| Classification | Ingredient | Weight Percent |
| --- | --- | --- |
| oil | cyclomethicone | 26.0 |
| moisturizers | squalane | 15.7 |
| | isopropyl myristate | 3.0 |
| sunscreens | p-(2-ethylhexyl)-dimethylaminobenzoate | 3.0 |
| | benzophenone-3 | 2.0 |
| skin humectants | water | 24.8 |
| surfactants | polysorbate 21 | 24.8 |
| | sodium dodecyl sulfate | 0.2 |
| preservatives | methylparaben | 0.15 |
| | propylparaben | 0.15 |
| | imidazolidinyl urea | 0.2 |

14. The composition of claim 1 in which the surfactants are non-ionic.

15. The composition of claim 2 in which the surfactants and non-ionic.

16. The composition of claim 8 in which the surfactants are non-ionic.

17. The composition of claim 9 in which the surfactants are non-ionic.

18. A composition according to claim 1 in which the content of skin humectants is from about 5% by weight to about 35% by weight of the composition.

19. A composition according to claim 8 in which the content of skin humectants is from about 5% by weight to about 35% by weight of the composition.

20. A composition according to claim 19 in which the content of surfactants is greater than 20% by weight of the composition.

* * * * *

UNITED STATES PATENT AND TRADEMARK OFFICE
CERTIFICATE OF CORRECTION

PATENT NO. : 4,797,272

DATED : January 10, 1989

INVENTOR(S) : Linn, Edward E. & West, Michael P.

It is certified that error appears in the above-identified patent and that said Letters Patent is hereby corrected as shown below:

Col. 2, line 61, change "both (" to --both--.

Col. 3, line 25, change "-inoil" to ---in-oil--.

Col. 5, line 25, change "container" to --containers--.

Col. 5, line 54, change "the the" to --to the--.

Col. 6, line 38 change "(0.1%)" to --(0.15%)--.

Col. 8, line 60, change "ssentially" to --essentially--.

Col. 10, line 50, change "and" to --are--.

Signed and Sealed this

Twenty-ninth Day of August, 1989

*Attest:*

DONALD J. QUIGG

*Attesting Officer*   *Commissioner of Patents and Trademarks*